(12) United States Patent
Evans et al.

(10) Patent No.: US 7,144,886 B2
(45) Date of Patent: *Dec. 5, 2006

(54) DIPEPTIDYL PEPTIDASE IV (DP-IV) INHIBITORS AS ANTI-DIABETIC AGENTS

(75) Inventors: David M. Evans, Southampton (GB); Andre Tartar, Vitry-en-Artois (FR)

(73) Assignee: Ferring B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/491,288

(22) PCT Filed: Oct. 23, 2002

(86) PCT No.: PCT/GB02/04787

§ 371 (c)(1),
(2), (4) Date: Sep. 7, 2004

(87) PCT Pub. No.: WO03/035067

PCT Pub. Date: May 1, 2003

(65) Prior Publication Data
US 2005/0004205 A1 Jan. 6, 2005

(30) Foreign Application Priority Data
Oct. 23, 2001 (GB) .................................. 0125446.5

(51) Int. Cl.
A61K 31/497 (2006.01)
A61K 31/4439 (2006.01)
C07D 241/12 (2006.01)
C07D 401/12 (2006.01)

(52) U.S. Cl. ................. 514/255.06; 514/343; 544/406; 546/279.1

(58) Field of Classification Search ................. 544/406
See application file for complete search history.

(56) References Cited

U.S. PATENT DOCUMENTS 3,959,248 A * 5/1976 Veber et al. ................. 530/331
6,911,467 B1 * 6/2005 Evans ......................... 514/423

FOREIGN PATENT DOCUMENTS

| WO | WO 95 15309 A | 6/1995 |
|---|---|---|
| WO | WO 99 61431 A | 12/1999 |
| WO | WO 01 40180 A | 6/2001 |
| WO | WO 01 81304 A | 11/2001 |
| WO | WO 01 81337 A | 11/2001 |

OTHER PUBLICATIONS

Gaudron, Sandrine et al., "NAcSDKP Analogs Resistant to Angiotensin-Converting Enzyme", Journal of Medicinal Chemistry (1997), 40(4), XP002223609, pp. 3963-3968.

* cited by examiner

Primary Examiner—Joseph K. McKane
Assistant Examiner—Andrew B. Freistein
(74) Attorney, Agent, or Firm—Foley & Lardner LLP

(57) ABSTRACT

The present invention relates to a series of prodrugs of inhibitors of DP-IV with improved properties. The compounds can be used for the treatment of a number of human diseases, including impaired glucose tolerance and type II diabetes. The compounds of the invention are described by general formula (1); wherein $R^1$ is H or CN; $R^2$ is selected from $CH_2R^5$, $CH_2CH_2R^5$ and $C(R^3)(R^4)-X^2-(CH_2)_aR^5$; $R^3$ and $R^4$ are each independently selected from H and Me; $R^5$ is selected from $CON(R^6)(R^7)$, $N(R^8)C(=O)R^9$, $N(R^8)C(=S)R^9$, $N(R^8)SO_2R^{10}$ and $N(R^8)R^{10}$; $R^6$ and $R^7$ are each independently $R^{11}(CH_2)_b$ or together they are $-(CH_2)_2-Z-(CH_2)_2-$ or $CH_2-o-C_6H_4-Z-CH_2-$; $R^8$ is H or Me; $R^9$ is selected from $R^{11}(CH_2)_b$, $R^{11}(CH_2)_bO$ and $N(R^6)(R^7)$; $R^{10}$ is $R^{11}(CH_2)_b$; $R^{11}$ is selected from H, alkyl, optionally substituted aryl, optionally substituted aroyl, optionally substituted arylsulphonyl and optionally substituted heteroaryl; $R^{12}$ is selected from $H_2NCH(R^{13})CO$, $H_2NCH(R^{14})CONHCH(R^{15})CO$, $C(R^{16})=C(R^{17})COR^{18}$ and $R^{19}OCO$; $R^{13}$, $R^{14}$ and $R^{15}$ are selected from the side chains of the proteinaceous amino acids; $R^{16}$ is selected from H, lower alkyl ($C_1-C_6$) and phenyl; $R^{17}$ is selected from H and lower alkyl ($C_1-C_6$); $R^{18}$ is selected from H, lower alkyl ($C_1-C_6$), OH, O-(lower alkyl ($C_1-C_6$)) and phenyl; $R_{19}$ is selected from lower alkyl ($C_1-C_6$), optionally substituted phenyl and $R^{20}C(=O)OC(R^{21})(R^{22})$; $R^{20}$, $R^{21}$ and $R^{22}$ are each independently selected from H and lower alkyl ($C_1-C_6$); Z is selected from a covalent bond, $-(CH_2)_c-$, $-O-$, $-SO_d-$ and $-N(R^{10})-$; $X^1$ is S or $CH_2$; $X^2$ is O, S or $CH_2$; a is 1, 2 or 3; b is 0–3; c is 1 or 2; and d is 0, 1 or 2.

(1)

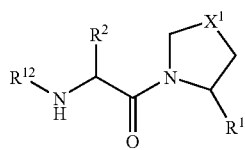

7 Claims, No Drawings

DIPEPTIDYL PEPTIDASE IV (DP-IV) INHIBITORS AS ANTI-DIABETIC AGENTS

The present invention relates to novel compounds that are prodrugs of inhibitors of dipeptidyl peptidase IV. The compounds are useful in the treatment of, inter alia, type 2 diabetes and impaired glucose tolerance.

BACKGROUND

The enzyme dipeptidyl peptidase IV, herein abbreviated DP-IV (and elsewhere as DAP-IV or DPP-IV) and also known by the classification EC.3.4.14.5, is a serine protease that cleaves the N-terminal dipeptide from peptides that begin with the sequence H-Xaa-Pro (where Xaa is any amino acid, although preferably a lipophilic one, and Pro is proline). It will also accept as substrates peptides that begin with the sequence H-Xaa-Ala (where Ala is alanine). DP-IV was first identified as a membrane-bound protein. More recently a soluble form has been identified.

Initial interest in DP-IV focussed on its role in the activation of T lymphocytes. DP-IV is identical to the T cell protein CD26. It was proposed that inhibitors of DP-IV would be capable of modulating T cell responsiveness, and so could be developed as novel immunomodulators. It was further suggested that CD26 was a necessary co-receptor for HIV, and thus that DP-IV inhibitors could be useful in the treatment of AIDS.

Attention was given to the role of DP-IV outside the immune system. It was recognised that DP-IV has a key role in the degradation of several peptide hormones, including growth hormone releasing hormone (GHRH) and glucagon-like peptide-1 and -2 (GLP-1 and GLP-2). Since GLP-1 is known to have a potentiating effect on the action of insulin in the control of post-prandial blood glucose levels it is clear that DP-IV inhibitors might also be usefully employed in the treatment of type II diabetes and impaired glucose tolerance. At least two DP-IV inhibitors are currently undergoing clinical trials to explore this possibility.

Several groups have disclosed inhibitors of DP-IV. While some leads have been found from random screening programs, the majority of the work in this field has been directed towards the investigation of substrate analogues. Inhibitors of DP-IV that are substrate analogues are disclosed in, for example, U.S. Pat. No. 5,462,928, U.S. Pat. No. 5,543,396, WO95/15309 (equivalent to U.S. Pat. No. 5,939,560 and EP 0731789), WO98/19998 (equivalent to U.S. Pat. No. 6,011,155), WO99/46272 and WO99/61431. The most potent inhibitors are aminoacyl pyrrolidine boronic acids, but these are unstable and tend to cyclise, while the more stable pyrrolidine and thiazolidine derivatives have a lower affinity for the enzyme and so would require large doses in a clinical situation. Pyrrolidine nitriles appear to offer a good compromise since they have both a high affinity for the enzyme and a reasonably long half-life in solution as the free base. There remains, however, a need for inhibitors of DP-IV with improved properties.

SUMMARY OF THE INVENTION

The present invention relates to a series of prodrugs of inhibitors of DP-IV with improved properties. The compounds can be used for the treatment of a number of human diseases, including impaired glucose tolerance and type II diabetes. Accordingly, the invention further relates to the use of the compounds in the preparation of pharmaceutical compositions, to such compositions per se, and to the use of such compositions in human therapy. The compounds of the invention are described by general formula 1.

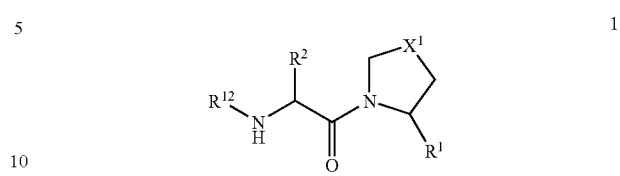

In this general formula $R^1$ is H or CN; $R^2$ is selected from $CH_2R^5$, $CH_2CH_2R^5$ and $C(R^3)(R^4)$—$X^2$—$(CH_2)_aR^5$; $R^3$ and $R^4$ are each independently selected from H and Me; $R^5$ is selected from $CON(R^6)(R^7)$, $N(R^8)C(\!=\!O)R^9$, $N(R^8)C(\!=\!S)R^9$, $N(R^8)SO_2R^{10}$ and $N(R^8)R^{10}$; $R^6$ and $R^7$ are each independently $R^{11}(CH_2)_b$ or together they are —$(CH_2)_2$—Z—$(CH_2)_2$— or —$CH_2$—o—$C_6H_4$—Z—$CH_2$—; $R^8$ is H or Me; $R^9$ is selected from $R^{11}$ $(CH_2)_b$, $R^{11}(CH_2)_bO$ and $N(R^6)(R^7)$; $R^{10}$ is $R^{11}(CH_2)_b$; $R^{11}$ is selected from H, alkyl, optionally substituted aryl, optionally substituted aryl, optionally substituted arylsulphonyl and optionally substituted heteroaryl; $R^{12}$ is selected from $H_2NCH(R^{13})CO$, $H_2NCH(R^{14})CONHCH(R^{15})CO$, $C(R^{16})\!=\!C(R^{17})COR^{18}$ and $R^{19}OCO$; $R^{13}$, $R^{14}$ and $R^{15}$ are selected from the side chains of the proteinaceous amino acids; $R^{16}$ is selected from H, lower alkyl ($C_1$–$C_6$) and phenyl; $R^{17}$ is selected from H and lower alkyl ($C_1$–$C_6$); $R^{18}$ is selected from H, lower alkyl ($C_1$–$C_6$), OH, O-(lower alkyl ($C_1$–$C_6$)) and phenyl; $R^{19}$ is selected from lower alkyl ($C_1$–$C_6$), optionally substituted phenyl and $R^{20}C(\!=\!O)OC(R^{21})(R^{22})$; $R^{20}$, $R^{21}$ and $R^{22}$ are each independently selected from H and lower alkyl ($C_1$–$C_6$); Z is selected from a covalent bond, —$(CH_2)_c$—, —O—, —$SO_d$— and —$N(R^{10})$—; $X^1$ is S or $CH_2$; $X^2$ is O, S or $CH_2$; a is 1, 2 or 3; b is 0–3; c is 1 or 2; and d is 0, 1 or 2.

DETAILED DESCRIPTION OF THE INVENTION

In a first aspect, the present invention relates to a series of novel compounds that are prodrugs of inhibitors of DP-IV with improved properties. The compounds of the invention are described by general formula 1.

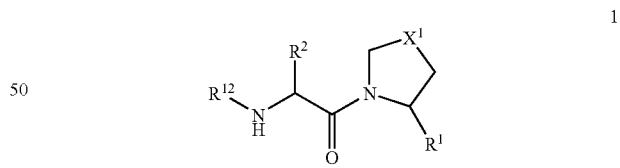

In this general formula $R^1$ is either a hydrogen atom (H) or a nitrile group (—CN) and $X^1$ is either a sulphur atom (S) or $CH_2$. In one preferred embodiment of the invention, $R^1$ is H. In another preferred embodiment, $R^1$ is CN.

$R^2$ is selected from a group according to $CH_2R^5$, a group according to $CH_2CH_2R^5$ and a group according to $C(R^3)(R^4)$—$X^2$—$(CH_2)_aR^5$, where $R^3$ and $R^4$ are each independently selected from H and a methyl group (Me), $X^2$ is O, S or $CH_2$ and a is 1, 2 or 3. Preferably $R^2$ is selected from a group according to $CH_2CH_2R^5$ and a group according to $C(R^3)(R^4)$—$X^2$—$(CH_2)_aR^5$. More preferably $R^2$ is selected from a group according to $CH_2CH_2R^5$ and a group according to $C(R^3)(R^4)$—$X^2$—$(CH_2)_aR^5$ where $R^3$ and $R^4$ are both H, $X^2$ is $CH_2$ and a is 1 or 2. Most preferably $R^2$ is selected from a group according to $CH_2CH_2CH_2R^5$ and a group according to $CH_2CH_2CH_2CH_2R^5$.

$R^5$ is selected from a group according to $CON(R^6)(R^7)$, a group according to $N(R^8)C(=O)R^9$, a group according to $N(R^8)C(=S)R^9$, a group according to $N(R^8)SO_2R^{10}$ and a group according to $N(R^8)R^{10}$. In one preferred embodiment of the invention, $R^5$ is a group according to $CON(R^6)(R^7)$. In another preferred embodiment, $R^5$ is selected from a group according to $N(R^8)C(=O)R^9$, a group according to $N(R^8)C(=S)R^9$, a group according to $N(R^8)SO_2R^{10}$ and a group according to $N(R^8)R^{10}$.

$R^6$ and $R^7$ may each independently a group according to $R^{11}(CH_2)_b$, where b is 0–3. Alternatively they may together be a chain —$(CH_2)_2$—Z—$(CH_2)_2$— or —$CH_2$—$C_6H_4$—Z—$CH_2$—, where Z is selected from a covalent bond, —$(CH_2)_c$—, —O—, —$SO_d$— and —$N(R^{10})$—, c is 1 or 2; and d is 0, 1 or 2, such that, together with the nitrogen atom to which they are attached, they form a five-, six- or seven-membered ring.

$R^8$ is H or Me.

$R^9$ is selected from a group according to $R^{11}(CH_2)_b$, a group according to $R^{11}(CH_2)_bO$ and a group according to $N(R^6)(R^7)$.

$R^{10}$ is a group according to $R^{11}(CH_2)_b$.

$R^{11}$ is selected from H, alkyl, optionally substituted aryl, optionally substituted aroyl, optionally substituted arylsulphonyl and optionally substituted heteroaryl.

The term alkyl, as used herein, denotes saturated hydrocarbon groups with between 1 and 10 carbon atoms, including straight-chain, branched and mono- and polycycloalkyl groups, such as methyl, ethyl, propyl, isopropyl, n-butyl, tert-butyl, cyclopentyl, cyclohexyl, cyclohexylmethyl, 2-cyclohexyl-2-propyl, bicyclo[2.2.2]octyl and the like.

The term aryl, as used herein, denotes monocyclic and fused bicyclic aromatic groups, including carbocyclic groups, such as phenyl and naphthyl, and heteroaryl groups with up to three heteroatoms selected from nitrogen, oxygen and sulphur, such as pyrrolyl, furyl, thienyl, pyrazolyl, imidazolyl, oxazolyl, isothiazolyl, pyridyl, pyrimidinyl, indolyl, quinolinyl and the like. Unless otherwise specified, an aryl, aroyl, arylsulphonyl or heteroaryl group may optionally be substituted with up to three groups independently selected from alkyl, OH, alkoxy, O-alkyl, Cl, F, Br, $NH_2$, amino (including alkylamino NH-alkyl and dialkylamino $N(alkyl)_2$), $CO_2H$, $CO_2$-alkyl, $CONH_2$, CONH-alkyl, CON(alkyl)$_2$, acyl, carboxy, carboxyalkyl, carboxamido, $NO_2$ and CN.

$R^{12}$ is selected from a group according to $H_2NCH(R^{13})CO$, a group according to $H_2NCH(R^{14})CONHCH(R^{15})CO$, a group according to $C(R^{16})=C(R^{17})COR^{18}$ and a group according to $R^{19}OCO$. In one preferred embodiment of the invention $R^{12}$ is selected from a group according to $H_2NCH(R^{13})CO$ and a group according to $H_2NCH(R^{14})CONHCH(R^{15})CO$. In another preferred embodiment of the invention $R^{12}$ is a group according to $R^{19}OCO$.

$R^{13}$, $R^{14}$ and $R^{15}$ are selected from the side chains of the proteinaceous amino acids, as listed in the following Table.

| Amino acid | Side chain |
| --- | --- |
| Alanine | —$CH_3$ |
| Arginine | —$(CH_2)_3NHC(:NH)NH_2$ |
| Asparagine | —$CH_2CONH_2$ |
| Aspartic acid | —$CH_2CO_2H$ |

-continued

| Amino acid | Side chain |
| --- | --- |
| Cysteine | —$CH_2SH$ |
| Glutamic acid | —$CH_2CH_2CO_2H$ |
| Glutamine | —$CH_2CH_2CONH_2$ |
| Glycine | —H |
| Histidine | 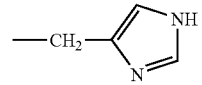 |
| Isoleucine | —$CH(CH_3)CH_2CH_3$ |
| Leucine | —$CH_2CH(CH_3)_2$ |
| Lysine | —$(CH_2)_4NH_2$ |
| Methionine | —$CH_2CH_2SCH_3$ |
| Phenylalanine | 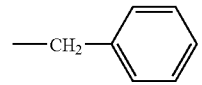 |
| Serine | —$CH_2OH$ |
| Threonine | —$CH_2CH(OH)CH_3$ |
| Tryptophan | 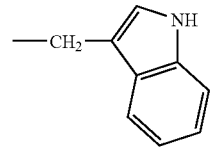 |
| Tyrosine | 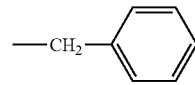 |
| Valine | —$CH(CH_3)_2$ |

$R^{16}$ is selected from H, lower alkyl ($C_1$–$C_6$ alkyl) and phenyl.

$R^{17}$ is selected from H and lower alkyl ($C_1$–$C_6$).

$R^{18}$ is selected from H, lower alkyl ($C_1$–$C_6$), OH, O-(lower alkyl ($C_1$–$C_6$)) and phenyl.

$R^{19}$ is selected from lower alkyl ($C_1$–$C_6$), optionally substituted phenyl and $R^{20}C(=O)OC(R^{21})(R^{22})$.

$R^{20}$, $R^{21}$ and $R^{22}$ are each independently selected from H and lower alkyl ($C_1$–$C_6$).

In a preferred embodiment, $X^1$ is $CH_2$ and $R^1$ is CN. For this embodiment, preferred $R^5$ groups are $CON(R^6)(R^7)$, $N(R^8)C(=O)R^9$, $N(R^8)C(=S)R^9$ and $N(R^8)R^{10}$. In another preferred embodiment, $X^1$ is $CH_2$ and $R^1$ is H. In another preferred embodiment $X^1$ is S. In a further preferred embodiment $X^1$ is S and $R^1$ is H.

Preferred compositions according to the invention may have improved activity and/or improved pharmacological profile. Preferred compositions may have in vivo stability characteristics which make them particularly suitable for use as pro-drugs.

Certain of the compounds of the present invention have acidic or basic properties and so can exist as salts. Insofar as such salts are non-toxic and otherwise pharmaceutically acceptable, they are included within the scope of the invention. Examples of such salts include, but are not limited to, the acetate, hydrochloride, sulphate, phosphate and benzoate salts of basic compounds, and the sodium, potassium and tetra-alkyl ammonium salts of acidic compounds.

Following administration, the compounds of the present invention are transformed into compounds according to general formula 2. These compounds are potent inhibitors of dipeptidyl peptidase IV.

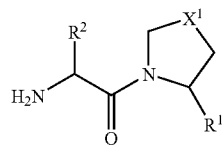

2

Accordingly, the compounds of the invention can be used for the treatment of a number of human diseases, including impaired glucose tolerance and type II diabetes. Further aspects of the invention therefore relate to the use of the compounds in the preparation of pharmaceutical compositions, to such compositions per se, and to the use of such compositions in human therapy.

The compounds of the present invention may be prepared according to methods that are well known in the field of organic chemistry, and particularly peptide chemistry. One strategy is to prepare the corresponding primary amine according to general formula 2 and then derivatise this.

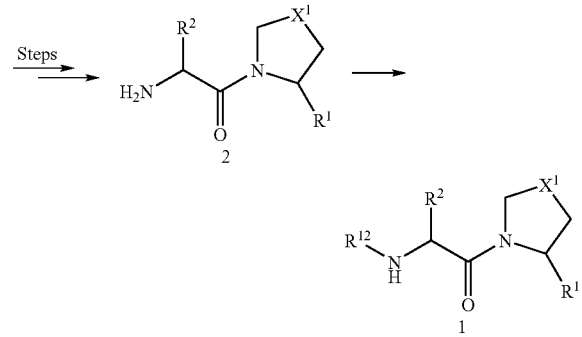

When $R^{12}$ is $H_2NCH(R^{13})CO$ then the final transformation may be accomplished in two steps by the reaction of 2 with a protected amino acid derivative followed by a deprotection step.

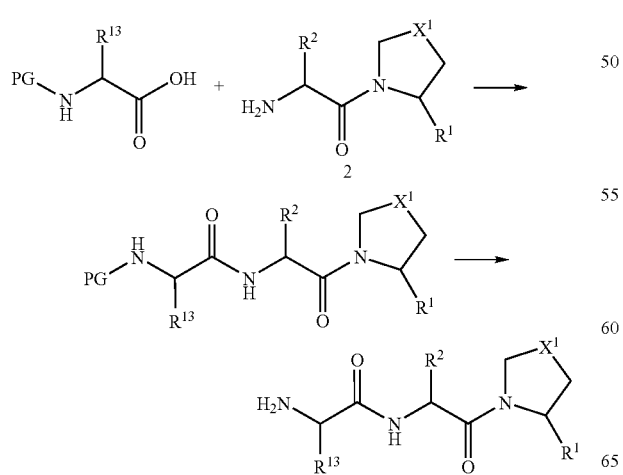

In the above scheme, PG is a protecting group such as tert-butyloxycarbonyl (BOC), 9-fluorenylmethyloxycarbonyl (FMOC) or benzyloxycarbonyl.

When $R^{12}$ is $H_2NCH(R^{14})CONHCH(R^{15})CO$ then the final transformation may be accomplished analogously by the reaction of 2 with a protected dipeptide derivative followed by a deprotection step, or in a slightly longer way with two cycles of coupling and deprotection.

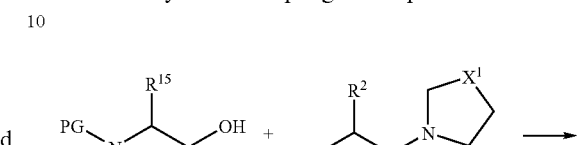
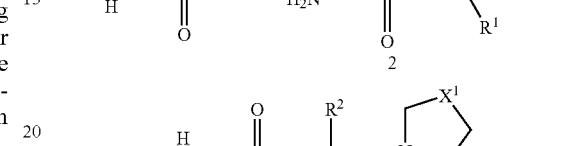
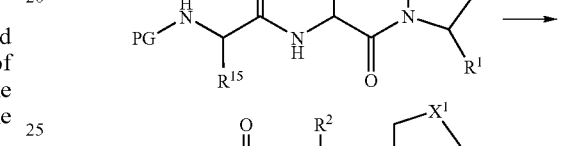
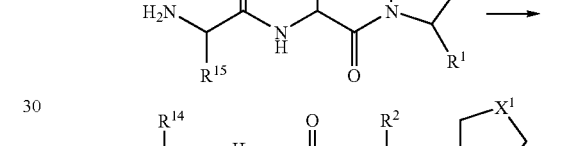
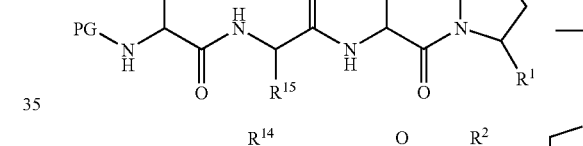
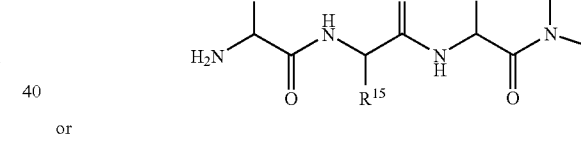

or

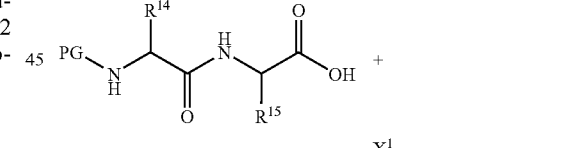
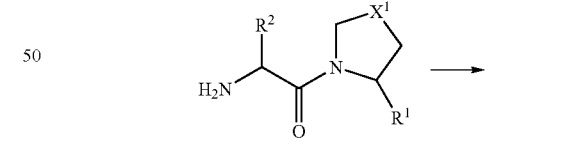
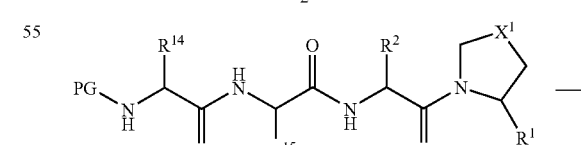
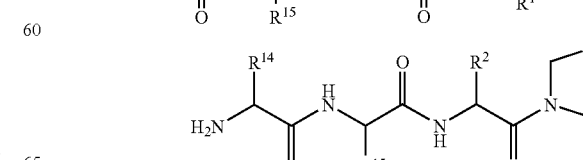

When $R^{12}$ is $C(R^{16})=C(R^{17})COR^{18}$ then the final transformation may be accomplished by the reaction of 2 with a suitable 1,3-dicarbonyl compound.

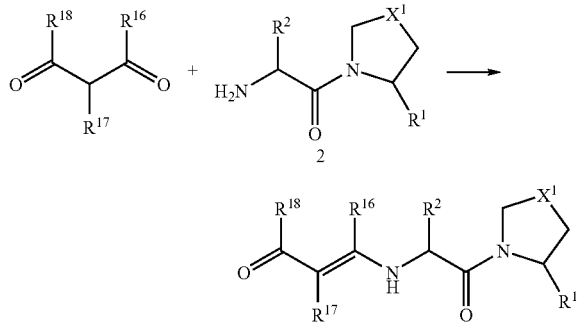

When $R^{12}$ is $R^{19}OCO$ then the final transformation may be accomplished by the reaction of 2 with a suitable active carbonic acid half ester derivative, such as a chloroformate or a para-nitrophenyl carbonate.

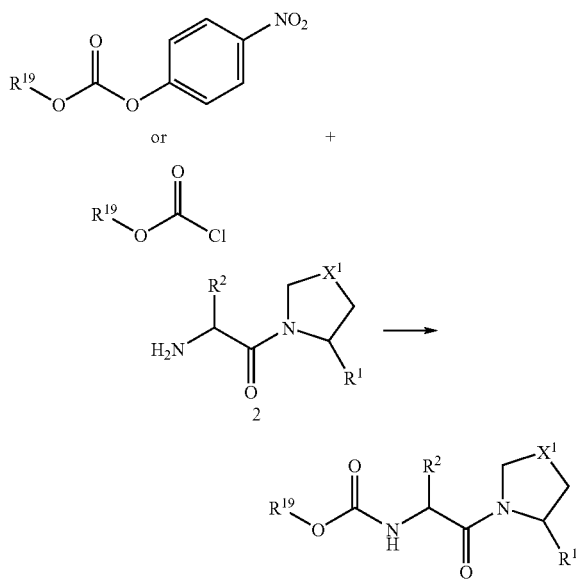

The intermediate 2 may be prepared by the coupling of a protected amino acid with a pyrrolidine or thiazolidine derivative, followed by a deprotection step.

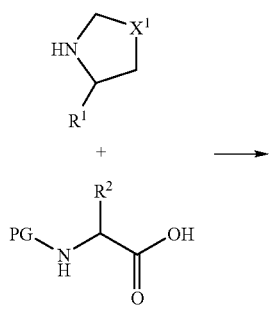

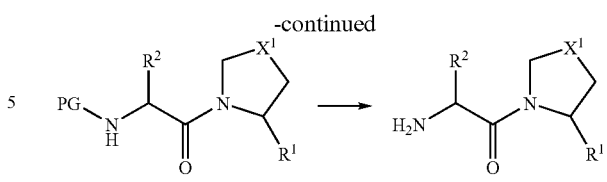

Alternatively, it may be more convenient to elaborate the functionality of $R^2$ after the assembly of the backbone of 2.

These general methods are further illustrated in the following non-limiting Examples.

EXAMPLE 1

(2S)-1-[N$^\alpha$-(1'-Acetoxyethoxycarbonyl)-N$^\omega$-(pyrazinyl-2-carbonyl)-L-ornithinyl]-pyrrolidine-2-carbonitrile

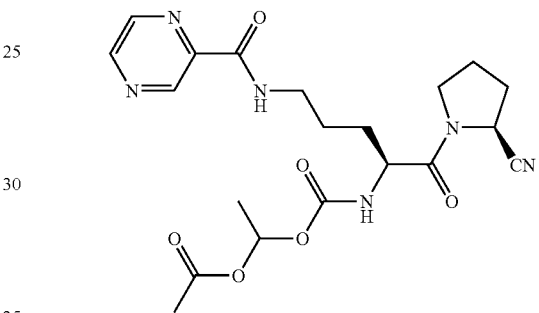

1A. N-(2-Nitrobenzenesulphenyl)-L-proline

L-Proline (25 g, 217 mmol) was dissolved in 2M NaOH (110 ml, 220 mmol) and dioxan (120 ml). A solution of 2-nitrobenzenesulphenyl chloride (42 g, 222 mmol) in dioxan (60 ml) was slowly added at the same time as 2M NaOH (110 ml, 220 mmol). The mixture was stirred for 2 hours at room temperature then poured into water (500 ml). The solid was removed by filtration. The pH of the filtrate was adjusted to pH3 with 2M HCl and the solution was extracted with ethyl acetate (3×500 ml). The combined organic extracts were washed with water (4×200 ml) and brine (1×200 ml), dried (Na$_2$SO$_4$) and evaporated in vacuo to give an orange solid identified as N-(2-nitrobenzenesulphenyl)-L-proline (58.1 g, 217 mmol, 100%).

1B. N-(2-Nitrobenzenesulphenyl)-L-proline succinimidyl ester

N-(2-Nitrobenzenesulphenyl)-L-proline (57.9 g, 216 mmol) was dissolved in CH$_2$Cl$_2$/DMF (9:1, 500 ml). N-Hydroxysuccinimide (37.3 g, 324 mmol) and water-soluble carbodiimide (51.8 g, 260 mmol) were added. The mixture was stirred for 18 hours at room temperature then the solvent was removed in vacuo and the residue was taken up in ethyl acetate (1000 ml). The solution was washed with water (4×200 ml) and brine (1×200 ml), dried (Na$_2$SO$_4$) and evaporated in vacuo to give a yellow solid identified as N-(2-nitrobenzenesulphenyl)-L-proline succinimidyl ester (78.9 g, 216 mmol, 100%).

1C. N-(2-Nitrobenzenesulphenyl)-L-prolinamide

N-(2-Nitrobenzenesulphenyl)-L-proline succinimidyl ester (78.5 g, 215 mmol) was dissolved in dioxan (500 ml). Ammonia (35%, 100 ml) was added. The mixture was stirred at room temperature for 2 hours then poured into water (700 ml). The precipitate was collected, washed with water (200 ml), dried over $P_2O_5$ and recrystallised from ethyl acetate/pet ether 60–80 to give a yellow solid identified as N-(2-nitrobenzenesulphenyl)-L-prolinamide (49.6 g, 185 mmol, 86%).

1D. (2S)-1-(2-Nitrobenzenesulphenyl)pyrrolidine-2-carbonitrile

N-(2-Nitrobenzenesulphenyl)-L-prolinamide (49 g, 183 mmol) was dissolved in dry THF (300 ml). The solution was cooled to 0° C., triethylamine (36.7 g, 367 mmol) was added followed by the slow addition of trifluoroacetic anhydride (77 g, 367 mmol). The pH was adjusted to pH9 with triethylamine. The mixture was stirred for 30 min then diluted with ethyl acetate (500 ml), washed with water (1×200 ml) and brine (1×200 ml), dried ($Na_2SO_4$) and evaporated in vacuo to give an orange oil which was purified by flash chromatography on silica gel (eluant: 80% pet ether 60–80, 20% ethyl acetate) to give a yellow solid identified as (2S)-1-(2-nitrobenzenesulphenyl)pyrrolidine-2-carbonitrile (38.9 g, 150 mmol, 82%).

1E. (2S)-Pyrrolidine-2-carbonitrile hydrochloride (2S)-1-(2-nitrobenzenesulphenyl)pyrrolidine-2-carbonitrile (38.5 g, 149 mmol) was dissolved in diethyl ether (200 ml). 4M HCl/Dioxan (150 ml, 600 mmol) was slowly added. The mixture was stirred for 2 h at room temperature then poured into diethyl ether (1000 ml). The solid was collected, washed with diethyl ether (500 ml) and recrystallised from methanol/diethyl ether to give a white solid identified as (2S)-pyrrolidine-2-carbonitrile hydrochloride (18.9 g, 142.5 mmol, 96%).

1F. (2S)-1-[$N^\alpha$-tert-Butyloxycarbonyl)-$N^\omega$-(pyrazinyl-2-carbonyl)-L-ornithinyl]-pyrrolidine-2carbonitrile $N^\alpha$-(tert-Butyloxycarbonyl)-$N^\omega$-(pyrazinyl-2-carbonyl)-L-ornithine (2.5 g, 7.4 mmol) was dissolved in $CH_2Cl_2$ (50 ml). This solution was cooled to 0° C., (2S)-pyrrolidine-2-carbonitrile hydrochloride (1.2 g, 9.1 mmol) and PyBOP (4.3 g, 8.23 mmol) were added, and the pH adjusted to pH9 with triethylamine. The mixture was stirred for 18 h at 0° C. to room temperature then the solvent was removed in vacuo and the residue was taken up in ethyl acetate (200 ml). The solution was washed with 0.3M $KHSO_4$ (2×50 ml), sat. $NaHCO_3$ (2×50 ml), water (2×50 ml) and brine (1×50 ml), dried ($Na_2SO_4$) and evaporated in vacuo to give a yellow oil which was purified by flash chromatography on silica gel (eluant: 80% ethyl acetate, 20% pet. ether, 60–80) to give a colourless oil identified as (2S)-1-[$N^\alpha$-(tert-butyloxycarbonyl)-$N^\omega$-(pyrazinyl-2-carbonyl)-L-ornithinyl]-pyrrolidine-2-carbonitrile (2.98 g, 7.16 mmol, 97%).

1G. (2S)-1-[$N^\alpha$-(Pyrazinyl-2-carbonyl)-L-ornithinyl]pyrrolidine-2-carbonitrile trifluoroacetate (2S)-1-[$N^\alpha$-tert-Butyloxycarbonyl-$N^\omega$-(pyrazinyl-2-carbonyl)-L-ornithinyl]pyrrolidine-2-carbonitrile (2.8 g, 6.7 mmol) was dissolved in trifluoroacetic acid (5 ml). The mixture was stirred for 1 hour at room temperature then the solvent was removed in vacuo to give a colourless oil identified as (2S)-1-[$N^\omega$-(pyrazinyl-2-carbonyl)-L-ornithinyl]pyrrolidine-2-carbonitrile trifluoroacetate (1.5 g, 3.48 mmol, 52%).

1H. (2S)-1-[$N^\alpha$-(1'-Acetoxyethoxycarbonyl)-$N^\omega$-(pyrazinyl-2-carbonyl)-L-ornithinyl]-pyrrolidine-2-carbonitrile A solution of (2S)-1-[$N^\omega$-(pyrazinyl-2-carbonyl)-L-ornithinyl]pyrrolidine-2-carbonitrile trifluoroacetate (200 mg, 0.47 mmol), α-acetoxyethyl p-nitrophenyl carbonate (140 mg, 0.52 mmol; prepared according to Alexander et al., J. Med. Chem. 31, 318, 1988) and triethylamine (60 mg, 0.6 mmol) in dichloromethane (25 ml) was stirred at room temperature for 18 hours then evaporated in vacuo. The residue was taken up in ethyl acetate (70 ml). The solution was washed with sat $NaHCO_3$, water and brine, dried ($Na_2SO_4$) and evaporated. The residue was purified by flash chromatography on silica gel (eluant: 98% chloroform, 2% methanol) to give a white solid identified as (2S)-1-[$N^\alpha$-(1'-acetoxyethoxycarbonyl)-$N^\omega$-(pyrazinyl-2-carbonyl)-L-ornithinyl]pyrrolidine-2-carbonitrile (30 mg, 0.07 mmol, 14%).

[M+H]$^+$=447.2 $^1$H NMR ($CDCl_3$): δ 1.41–1.48 (3H,m), 1.72–1.86 (4H,m), 2.02 (3H,d,J=7.7 Hz), 2.11–2.28 (4H,m), 3.51–3.57 (2H,m), 3.68–3.69 (2H,m), 4.47–4.48 (1H,m), 4.74–4.76 (1H,m), 5.55–5.59 (1H,m), 6.75–6.78 (1H,m), 7.89–7.91 (1H,m), 8.52 (1H,d,J=1.9 Hz), 8.76 (1H,d,J=2.5 Hz), 9.3 (1H,d,J=1.5 Hz) ppm.

EXAMPLE 2

(4R)-3-[$N^\alpha$-Methoxycarbonyl)-$N^\omega$-(pyrazinyl-2-carbonyl)-L-lysinyl]thiazolidine-4-carbonitrile

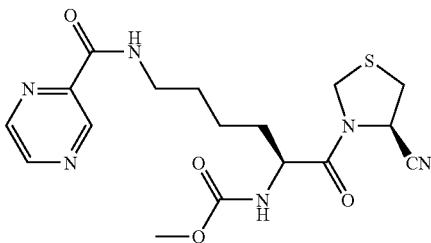

2A. (4R)-3-(tert-Butyloxycarbonyl)thiazolidine-4-carboxamide (4R)-3-(tert-Butyloxycarbonyl)thiazolidine-4-carboxylic acid (12.5 g, 54.1 mmol) was dissolved in $CH_2Cl_2$/DMF (9:1, 150 ml). To this solution at 0° C. was added 1-hydroxybenzotriazole hydrate (14.6 g, 108 mmol) and water-soluble carbodiimide (13.0 g, 65 mmol). The mixture was stirred for 1 hour at 0° C. then ammonia (35%, 50 ml) was added. The mixture was stirred for 18 h at 0° C. to room temperature then the solvent was removed in vacuo and the residue was taken up in ethyl acetate (500 ml). The solution was washed with 0.3M $KHSO_4$ (2×100 ml), sat. $NaHCO_3$ (2×100 ml), water (2×100 ml) and brine (1×100 ml), dried ($Na_2SO_4$) and evaporated in vacuo to give a yellow oil. The residue was purified by flash chromatography on silica gel (eluant: 2% methanol, 98% chloroform) to give a colourless oil identified as (4R)-3-(tert-butyloxycarbonyl)thiazolidine-4-carboxamide (8.9 g, 38.4 mmol,71%).

2B. (4R)-Thiazolidine-4-carboxamide hydrochloride (4S)-3(tert-Butyloxycarbonyl)thiazolidine-4-carboxamide (8.6 g, 37.1 mmol) was dissolved in 4M HCl/dioxan (50 ml). The mixture was stirred for 1 hour at room temperature then the solvent was evaporated in vacuo to give a white solid identified as (4R)-thiazolidinecarboxamide hydrochloride (6.2 g, 36.8 mmol, 99%).

2C. (4R)-3-[$N^\alpha$-tert-Butyloxycarbonyl)-$N^\omega$-(9-fluorenylmethyloxycarbonyl)-L-lysinyl]thiazolidine-4-carboxamide $N^\alpha$-(tert-Butyloxycarbonyl)-$N^\omega$-(9-fluorenylmethyloxycarbonyl)-L-lysine (5 g, 10.7 mmol) was dissolved in $CH_2Cl_2$ (100 ml). This solution was cooled to 0° C., (4R)-thiazolidine-4-carboxamide hydrochloride (1.78 g, 11.7 mmol) and PyBOP (6.7 g, 12.8 mmol) were added, and the pH was adjusted to pH9 with triethylamine. The mixture was stirred for 18 h at 0° C. to room temperature then the solvent was removed in vacuo and the residue was taken up in ethyl acetate (200 ml). The solution was washed with 0.3M $KHSO_4$ (2×50 ml), sat. $NaHCO_3$ (2×50 ml), water (2×50 ml) and brine (1×50 ml), ($Na_2SO_4$) and evaporated in vacuo to give a yellow oil. The residue was purified by flash chromatography on silica gel (eluant: 2% methanol, 98% chloroform) to give a colourless oil identified as (4R)-3-[$N^\alpha$-(tert-butyloxycarbonyl)-$N^\omega$-(9-fluorenylmethyloxycarbonyl)-L-lysinyl]thiazolidine-4carboxamide (2.81 g, 4.8 mmol, 44%).

2D. (4R)-3-[$N^\alpha$-(tert-Butyloxycarbonyl)-$N^\omega$-(9-fluorenylmethyloxycarbonyl)-L-lysinyl]thiazolidine-4-carbonitrile (4R)-3-[$N^\alpha$-(tert-Butyloxycarbonyl)-$N^\omega$-(9-fluorenylmethyloxycarbonyl)-L-lysinyl]-thiazolidine-4-carboxamide (2.7 g, 4.7 mmol) was dissolved in dry THF (100 ml). The solution was cooled to 0° C. and triethylamine (1.0 g, 10 mmol) was added followed by the slow addition of trifluoroacetic anhydride (2.0 g, 9.5 mmol). The pH was adjusted to pH9 with triethylamine. The mixture was stirred for 30 min then diluted with ethyl acetate (100 ml), washed with water (1×50 ml) and brine (1×50 ml), dried ($Na_2SO_4$) and evaporated in vacuo. The residue was purified by flash chromatography on silica gel (eluant: 60% pet ether 60–80, 40% ethyl acetate) to give a colourless oil identified as (4R)-3-[$N^\alpha$-(tert-butyloxycarbonyl)-$N^\omega$-(9-fluorenylmethyloxycarbonyl)-L-lysinyl]-thiazolidine-4-carbonitrile (2.14 g, 3.81 mmol, 82%).

2E. (4R)-3-[$N^\alpha$-(tert-Butyloxycarbonyl)-L-lysinyl]thiazolidine-4-carbonitrile (4R)-3-[$N^\alpha$-(tert-Butyloxycarbonyl)-$N^\omega$-(9-fluorenylmethyloxycarbonyl)-L-lysinyl]-thiazolidine-4-carbonitrile (1.9 g, 3.4 mmol) was dissolved in THF (40 ml). Diethylamine (10 ml) was added. The mixture was stirred for 2 h at room temperature then the solvent was removed in vacuo. The residue was purified by flash chromatography on silica gel (eluant: 90% chloroform, 7% methanol, 3% triethylamine) to give a colourless oil identified as (4R)-[$N^\alpha$-(tert-butyloxycarbonyl)-L-lysinyl]thiazolidine-4-carbonitrile (863 mg, 2.5 mmol, 75%).

2F. (4R)-3-[$N^\alpha$-(tert-Butyloxycarbonyl)-$N^\omega$-(pyrazinyl-2-carbonyl)-L-lysinyl]-thiazolidine-4-carbonitrile (4R)-3-[$N^\alpha$-(tert-Butyloxycarbonyl)-L-lysinyl]thiazolidine-4-carbonitrile (100 mg, 0.29 mmol) was dissolved in $CH_2Cl_2$ (20 ml). To this solution at 0° C. were added 2-pyrazinecarboxylic acid (43 mg, 0.35 mmol) and PyBOP (170 mg, 0.33 mmol) and the pH was adjusted to pH9 with triethylamine. The mixture was stirred for 18 h at 0° C. to room temperature then the solvent was removed in vacuo and the residue was taken up in ethyl acetate (70 ml). The solution was washed with 0.3M $KHSO_4$ (2×20 ml), sat. $NaHCO_3$ (2×20 ml), water (2×20 ml) and brine (1×20 ml), dried ($Na_2SO_4$) and evaporated in vacuo. The residue was purified by flash chromatography on silica gel (eluant: 2% methanol, 98% chloroform) to give a colourless oil identified as (4R)-3-[$N^\alpha$-(tert-butyloxycarbonyl)-$N^\omega$-(pyrazinyl-2-carbonyl)-L-lysinyl]thiazolidine-4-carbonitrile (112 mg, 0.25 mmol, 86%).

2G. (4R)-3-[$N^\alpha$-Methoxycarbonyl)-$N^\omega$-(pyrazinyl-2-carbonyl)-L-lysinyl]-thiazolidine-4-carbonitrile (4R)-3-[$N^\alpha$-(tert-Butyloxycarbonyl)-$N^\omega$-(pyrazinyl-2-carbonyl)-L-lysinyl]thiazolidine-4-carbonitrile (160 mg, 0.36 mmol) was dissolved in 4M HCl/dioxan (30 ml). The mixture was stirred for 1 hour at room temperature then the solvent was removed in vacuo. The residue was dissolved in dichloromethane (25 ml). Methyl chloroformate (50 mg, 0.53 mmol) and triethylamine (60 mg, 0.6 mmol) were added and the solution was stirred at room temperature for 18 hours then solution was evaporated in vacuo. The residue was taken up in ethyl acetate (70 ml). The solution was washed with sat $NaHCO_3$, water and brine, dried ($Na_2SO_4$) and evaporated. The residue was purified by flash chromatography on silica gel (eluant: 90% ethyl acetate: 10% pet. ether 60–80) to give a white solid identified as (4R)-3-[$N^\alpha$-methoxycarbonyl)-$N^\omega$-(pyrazinyl-2-carbonyl)-L-lysinyl]thiazolidine-4-carbonitrile (52 mg, 0.13 mmol, 35%).

$[M+H]^+$=407.1 $^1$H NMR ($CDCl_3$): δ 1.33–1.48 (4H,m), 1.63–1.82 (2H,m), 3.21–3.27 (2H,m), 3.45–3.60 (2H,m), 3.63 (3H,s), 4.44–4.46 (1H,m), 4.63 (1H,d,J=8.4 Hz), 4.86 (1H,d,J=8.5 Hz), 5.23–5.27 (1H,m), 5.53 (1H,d,J=8.2 Hz), 7.85–7.87 (1H,m), 8.50–8.51 (1H,m), 8.73 (1H,d,J=2.5 Hz), 9.38 (1H,d,J =1.3 Hz) ppm.

EXAMPLE 3

(4R)-3-[$N^\alpha$-(1'-Acetoxyethoxycarbonyl)-$N^\omega$-(3-cyanobenzenesulphonyl)-L ornithinyl]thiazolidine-4-carbonitrile

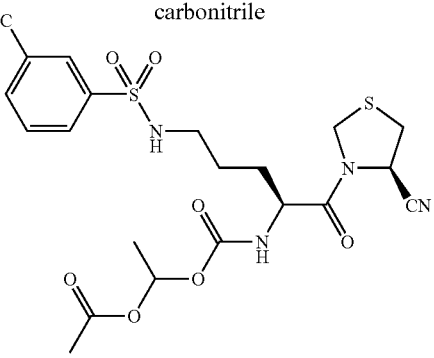

3A. (4R)-3-[$N^\alpha$-(tert-Butyloxycarbonyl)-$N^\omega$-(9-fluorenylmethyloxycarbonyl)-L-ornithinyl]thiazolidine-4-carboxamide N$^\alpha$-(tert-Butyloxycarbonyl)-N$^\omega$-(9fluorenylmethyloxycarbonyl)-L-ornithine (2.8 g, 6.2 mmol) was dissolved in CH$_2$Cl$_2$/DMF (9:1, 100 ml). This solution was cooled to 0° C., (4R)-thiazolidine-4-carboxamide hydrochloride (1.78 g, 11.7 mmol), 1-hydroxybenzotriazole hydrate (1.1 g, 8.1 mmol) and water-soluble carbodiimide (1.5 g, 7.5 mmol) were added, and the pH was adjusted to pH8 with N-methylmorpholine. The mixture was stirred for 18 h at 0° C. to room temperature then the solvent was removed in vacuo and the residue was taken up in ethyl acetate (200 ml). The solution was washed with 0.3M KHSO$_4$ (2×50 ml), sat. NaHCO$_3$ (2×50 ml), water (2×50 ml) and brine (1×50 ml), dried (Na$_2$SO$_4$) and evaporated in vacuo to give a yellow oil. The residue was purified by flash chromatography on silica gel (eluant: 85% ethyl acetate, 15% pet. ether 60–80) to give a colourless oil identified as (4R)-3-[N$^\alpha$-(tert-butyloxycarbonyl-N$^\omega$-(9-fluorenylmethyloxycarbonyl)-L-ornithinyl]thiazolidine-4-carboxamide (2.26 g, 3.9 mmol, 66%).

3B. (4R)-3-[N$^\alpha$-(tert-Butyloxycarbonyl)-N$^\omega$-(9-fluorenylmethyloxycarbonyl)-L-ornithinyl]thiazolidine-4-carbonitrile (4R)-3-[N$^\alpha$-(tert-Butyloxycarbonyl)-N$^\omega$-(9-fluorenylmethyloxycarbonyl)-L-ornithinyl]-thiazolidine-4-carboxamide (2.1 g, 3.7 mmol) was dissolved in dry THF (100 ml). The solution was cooled to 0° C., triethylamine (740 mg, 7.4 mmol) was added followed by the slow addition of trifluoroacetic anhydride (1.65 g, 7.9 mmol). The pH was adjusted to pH9 with triethylamine. The mixture was stirred for 30 min then diluted with ethyl acetate (100 ml), washed with water (1×50 ml) and brine (1×50 ml), dried (Na$_2$SO$_4$) and evaporated in vacuo. The residue was purified by flash chromatography on silica gel (eluant: 45% pet ether 60–80, 55% ethyl acetate) to give a colourless oil identified as (4R)-3-[N$^\alpha$-(tert-butyloxycarbonyl)-N$^\omega$-(9-fluorenylmethyloxycarbonyl)-L-ornithinyl]-thiazolidine-4-carbonitrile (1.73 g, 3.14 mmol, 85%).

3C. (4R)-3-[N$^\alpha$-(tert-Butyloxycarbonyl)-L-ornithinyl]thiazolidine-4-carbonitrile (4R)-3-[N$^\alpha$-(tert-Butyloxycarbonyl)-N$^\omega$-(9-fluorenylmethyloxycarbonyl)-L-ornithinyl]-thiazolidine-4-carbonitrile (1.6 g, 2.9 mmol) was dissolved in THF (40 ml). Diethylamine (10 ml) was added. The mixture was stirred for 2 h at room temperature then the solvent was removed in vacuo. The residue was purified by flash chromatography on silica gel (eluant: 90% chloroform, 7% methanol, 3% triethylamine) to give a colourless oil identified as (4R)-3-[N$^\alpha$-(tert-butyloxycarbonyl)-L-omithinyl]thiazolidine-4-carbonitrile (902 mg, 2.75 mmol, 95%).

3D. (4R)-3-[N$^\alpha$-(tert-Butyloxycarbonyl)-N$^\omega$-(3-cyanobenzenesulphonyl)-L-ornithinyl]thiazolidine-4-carbonitrile (4R)-3-[N$^\alpha$-(tert-Butyloxycarbonyl)-L-ornithinyl]thiazolidine-4-carbonitrile (207 mg, 0.63 mmol) was dissolved in CH$_2$Cl$_2$ (25 ml). To this solution at 0° C. was added 3-cyanobenzenesulphonyl chloride (135 mg, 0.67 mmol) and the pH was adjusted to pH9 with triethylamine. The mixture was stirred for 18 h at 0° C. to room temperature then the solvent was removed in vacuo and the residue was taken up in ethyl acetate (70 ml). The solution was washed with 0.3M KHSO$_4$ (2×20 ml), sat. NaHCO$_3$ (2×20 ml), water (2×20 ml) and brine (1×20 ml), dried (Na$_2$SO$_4$) and evaporated in vacuo. The residue was purified by flash chromatography on silica gel (eluant: 45% ethyl acetate: 55% pet. ether 60–80° C.) to give a colourless oil identified as (4R)-3-[N$^\alpha$-(tert-butyloxycarbonyl)-N$^\omega$-(3-cyanobenzenesulphonyl)-L-ornithinyl]thiazolidine-4-carbonitrile (162 mg, 0.33 mmol, 52%).

3E. (4R)-3-[N$^\alpha$-(1'-Acetoxyethoxycarbonyl)-N$^\omega$-(3-cyanobenzenesulphonyl)-L-ornithinyl]thiazolidine-4-carbonitrile (4R)-3-[N$^\alpha$-(tert-Butyloxycarbonyl)-N$^\omega$-(3-cyanobenzenesulphonyl)-L-ornithinyl]-thiazolidine-4-carbonitrile (142 mg, 0.29 mmol) was dissolved in trifluoroacetic acid (5 ml). The mixture was stirred for 1 hour at room temperature then the solvent was removed in vacuo. The residue was dissolved in dichloromethane (25 ml) and α-acetoxyethyl p-nitrophenyl carbonate (108 mg, 0.40 mmol; prepared according to Alexander et al., J. Med. Chem. 31, 318, 1988) and triethylamine (60 mg, 0.6 mmol) were added. The reaction was stirred at room temperature for 18 hours, then evaporated in vacuo. The residue taken up in ethyl acetate (70 ml) and the solution was washed with sat NaHCO$_3$, water and brine, dried (Na$_2$SO$_4$) and evaporated. The residue was purified by flash chromatography on silica gel (eluant: 70% ethyl acetate: 30% pet. ether 60–80) to give a white solid identified as (4R)-3-[N$^\alpha$-(1'-acetoxyethoxycarbonyl)-N$^\omega$-(3-cyanobenzenesulphonyl)-L-ornithinyl]thiazolidine-4-carbonitrile (32 mg, 0.06 mmol, 21%).

[M+H]$^+$=524.0 $^1$H NMR (CDCl$_3$): δ 1.20–1.22 (2H,m), 1.43–1.46 (3H,m), 1.59–1.78 (4H,m), 2.03–2.06 (3H,m), 3.03 (2H,d,J=4.2 Hz), 3.29–3.33 (2H,m), 4.61–4.66 (1H,m), 4.79–4.84 (1H,m), 5.16–5.20 (1H,m), 5.73–5.82 (1H,m), 6.74–6.76 (1H,m), 7.63–7.69 (1H,m), 7.83–7.86 (1H,m), 8.10–8.16 (2H,m) ppm.

EXAMPLE 4

(2S,2'S)-1-[2'-(1''-Acetoxyethoxycarbonylamino)-5'-oxo-5'-(tetrahydroisoquinoline-2-yl)pentanoyl]pyrrolidine-2-carbonitrile

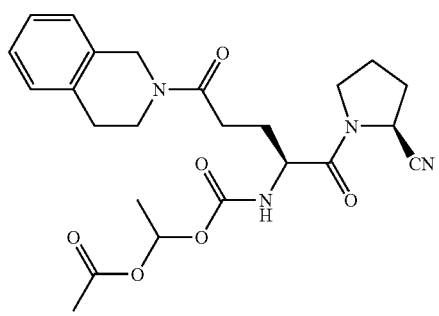

4A. (2S)-1-[N-(tert-Butyloxycarbonyl)-O$^\omega$-methyl-L-glutamyl]pyrrolidine-2-carbonitrile N-(tert-Butyloxycarbonyl)-O$^\omega$-methyl-L-glutamic acid (1.0 g, 3.83 mmol) was dissolved in CH$_2$Cl$_2$/DMF (9:1, 20 ml). To this solution at 0° C. were added 1-hydroxybenzotriazole hydrate (788 mg, 5.84 mmol), water-soluble carbodiimide (877 mg, 4.38 mmol), (2S)-pyrrolidine-2-carbonitrile hydrochloride (609 mg, 4.6 mmol) and triethylamine (65 mg, 0.65 mmol). The mixture was stirred for 18 h at 0° C. to room temperature then the solvent was removed in vacuo and the residue was taken up in ethyl acetate (70 ml). The solution was washed with 0.3M $KHSO_4$ (2×20 ml), sat. $NaHCO_3$ (2×20 ml), water (2×20 ml) and brine (1×20 ml), dried ($Na_2SO_4$) and evaporated in vacuo. The residue was purified by flash chromatography on silica gel (eluant: 50% ethyl acetate, 50% pet. ether 60–80) to give a brown oil identified as (2S)-1-[N-(tert-butyloxycarbonyl)-O$^\omega$-methyl-L-glutamyl]pyrrolidine-2-carbonitrile (290 mg, 0.86 mmol, 22%).

4B. (2S)-1-[N-(tert-Butyloxycarbonyl)-L-glutamy]pyrrolidine-2-carbonitrile (2S)-1-[N-(tert-Butyloxycarbonyl)-O$^\omega$-methyl-L-glutamyl]pyrrolidine-2-carbonitrile (250 mg, 0.74 mmol) was dissolved in dioxan (5 ml). 1M Lithium hydroxide (1.1 ml, 1.1 mmol) was added. The mixture was stirred for 1 hour at room temperature then the solvent was removed in vacuo and the residue was taken up in ethyl acetate (70 ml). The solution was washed with 1M $KHSO_4$ (2×20ml), water (2×20 ml) and brine (1×20ml), dried ($Na_2SO_4$) and evaporated in vacuo to give a colourless oil identified as (2S)-1-[N-(tert-butyloxycarbonyl)-L-glutamy]pyrrolidine-2-carbonitrile (200 mg, 0.61 mmol, 83%).

4C. (2S,2'S)-1-[2'-(tert-Butyloxycarbonylamino)-5'-oxo-5'-(tetrahydroisoquinolin-2-yl)pentanoyl]pyrrolidine-2-carbonitrile (2S)-1-[N-(tert-Butyloxycarbonyl)-L-glutamyl]pyrrolidine-2-carbonitrile (200 mg, 0.61 mmol) was dissolved in $CH_2Cl_2$/DMF (9:1, 20 ml). To this solution at 0° C. were added 1-hydroxybenzotriazole hydrate (98 mg, 0.73 mmol), water-soluble carbodiimide (140 mg, 0.73 mmol), tetrahydroisoquinoline (109 mg, 0.82 mmol) and triethylamine(150 mg, 1.5 mmol). The mixture was stirred for 18 h at 0° C. to room temperature then the solvent was removed in vacuo and the residue was taken up in ethyl acetate (70 ml). The solution was washed with 0.3M $KHSO_4$ (2×20 ml), sat. $NaHCO_3$ (2×20 ml), water (2×20 ml) and brine (1×20 ml), dried ($Na_2SO_4$) and evaporated in vacuo to give a yellow oil. The residue was purified by flash chromatography on silica gel (eluant: 5% methanol, 97% chloroform) to give a colourless oil identified as (2S,2'S)-1-[2'-(tert-butyloxycarbonylamino)-5'-oxo-5'-(tetrahydroisoquinolin-2-yl)pentanoyl] pyrrolidine-2-carbonitrile (149 mg, 0.34 mmol, 56%).

4D. (2S,2'S)-1-[2'-(1''-Acetoxyethoxycarbonylamino)-5'-oxo-5'-(tetrahydroisoquinolin-2-yl)pentanoyl]pyrrolidine-2carbonitrile (2S,2'S)-1-[2'-(tert-butyloxycarbonylamino)-5'-oxo-5'-(tetrahydroisoquinolin-2-yl)-pentanoyl]pyrrolidine-2-carbonitrile (149 mg, 0.34 mmol) was dissolved in trifluoroacetic acid (20 ml). The mixture was stirred for 1 hour at room temperature then the solvent was removed in vacuo. The residue was dissolved in dichloromethane (25 ml) and α-acetoxyethyl p-nitrophenyl carbonate (100 mg, 0.37 mmol; prepared according to Alexander et al., J. Med. Chem. 31, 318, 1988) and triethylamine (40 mg, 0.4 mmol) were added. The reaction was stirred at room temperature for 18 hours then evaporated in vacuo and the residue was taken up in ethyl acetate (70 ml). The solution was washed with sat $NaHCO_3$, water and brine, dried ($Na_2SO_4$) and evaporated. The residue was purified by flash chromatography on silica gel (eluant: 90% ethyl acetate, 10% pet. ether 60–800° C.) to give a white solid identified as (2S,2'S)-1-[2'-(1''-Acetoxyethoxycarbonylamino)-5'-oxo-5'-(tetrahydroisoquinolin-2-yl)pentanoyl]pyrrolidine-2-carbonitrile (58 mg, 0.12 mmol, 36%).

[M+H]$^+$=471.2 $^1$H NMR (CDCl$_3$): δ 1.40–1.44 (3H,m), 2.00–2.07 (3H,m), 2.13–2.40 (9H,m), 2.82–2.91 (2H,m), 3.63–3.70 (2H,m), 3.96–4.18 (1H,m), 4.57–4.61 (2H,m), 4.72–4.75 (2H,m), 5.78–5.80 (1H,m), 6.69–6.75 (1H,m), 7.10–7.25 (4H,m) ppm.

EXAMPLE 5

(2S)-1-[N$^\alpha$-(4'-Oxopent-2'-en-2'-yl)-N$^\omega$-(quinoxalinyl-2-carbonyl)-L-ornithinyl]-pyrrolidine-2-carbonitrile

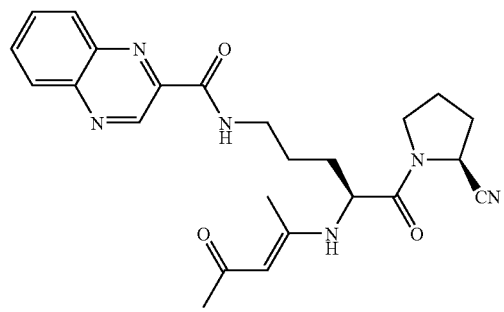

5A. 1-[N$^\alpha$-(tert-Butyloxycarbonyl)-N$^\omega$-(9-fluorenylmethyloxycarbonyl)-L-ornithinyl]-L-prolineamide N$^\alpha$-(tert-Butyloxycarbonyl)-N$^\omega$-(9-fluorenylmethyloxycarbonyl)-L-ornithine (5 g, 11.0 mmol) was dissolved in $CH_2Cl_2$ (40 ml). This solution was cooled to 0° C., L-prolineamide (1.4 g, 12.2 mmol) and PyBOP (6.3 g, 12.1 mmol) were added, and the pH was adjusted to pH9 with triethylamine. The mixture was stirred for 18 h at 0° C. to room temperature then the solvent was removed in vacuo and the residue was taken up in chloroform (200 ml). The solution was washed with 0.3M $KHSO_4$ (2×50 ml), sat. $NaHCO_3$ (2×50 ml), water (2×50 ml) and brine (1×50 ml), dried ($Na_2SO_4$) and evaporated in vacuo to give a yellow oil. The residue was purified by flash chromatography on silica gel (eluant: 98% chloroform, 2% methanol) to give a colourless oil identified as 3-[N$^\alpha$-(tert-butyloxycarbonyl)-N$^\omega$-(9-fluorenylmethyloxycarbonyl)-L-ornithinyl]-L-prolineamide (4.2 g, 7.6 mmol, 69%).

5B. (2S)-1-[N$^\alpha$-(tert-Butyloxycarbonyl)-N$^\omega$-(9-fluorenylmethyloxycarbonyl)-L-ornithinyl]pyrrolidine-2-carbonitrile N—[N$^\alpha$-(tert-Butyloxycarbonyl)-N$^\omega$-(9-fluorenylmethyloxycarbonyl)-L-ornithinyl]-L-prolineamide (4.1 g, 7.4 mmol) was dissolved in dry THF (100 ml). The solution was cooled to 0° C. and triethylamine (820 mg, 8.2 mmol) was added followed by the slow addition of trifluoroacetic anhydride (1.7 g, 8.1 mmol). The pH was adjusted to pH9 with triethylamine. The mixture was stirred for 30 min then diluted with ethyl acetate (100 ml), washed with water (1×50 ml) and brine (1×50 ml), dried ($Na_2SO_4$) and evaporated in vacuo. The residue was purified by flash chromatography on silica gel (eluant: 20% ethyl acetate, 80% pet. ether 60–80) to give a colourless oil identified as (2S)-1-[N$^\alpha$-(tert-butyloxycarbonyl)-N$^\omega$-(9-fluorenylmethyloxycarbonyl)-L-ornithinyl]pyrrolidine-2-carbonitrile (3.5 g, 6.5 mmol, 87%).

5C. (2S)-1-[N$^\alpha$-(tert-Butyloxycarbonyl)-L-ornithinyl]pyrrolidine-2-carbonitrile (2S)-1-[N$^\alpha$-(tert-Butyloxycarbonyl)-N$^\omega$-(9-fluorenylmethyloxycarbonyl)-L-ornithinyl]-pyrrolidine-2-carbonitrile (3.4 g, 6.4 mmol) was dissolved in THF (40 ml). Diethylamine (10 ml) was added. The mixture was stirred for 2 h at room temperature then the solvent was removed in vacuo. The residue was purified by flash chromatography on silica gel (eluant: 90% chloroform, 7% methanol, 3% triethylamine) to give a colourless oil identified as (2S)-1-[N$^\alpha$-(tert-butyloxycarbonyl)-L-ornithinyl]pyrrolidine-2-carbonitrile (1.48 g, 4.77 mmol, 75%).

5D. (2S)-1-[N$^\alpha$-tert-Butyloxycarbonyl)-N$^\omega$-(quinoxalinyl-2-carbonyl)-L-ornithinyl]-pyrrolidine-2-carbonitrile (2S)-1-[N$^\alpha$-(tert-Butyloxycarbonyl)-L-ornithinyl]pyrrolidine-2-carbonitrile (300 mg, 0.97 mmol) was dissolved in CH$_2$Cl$_2$ (25 ml). To this solution at 0° C. was added 2-quinoxaloyl chloride (200 mg, 1.04 mmol) and the pH was adjusted to pH9 with triethylamine. The mixture was stirred for 18 h at 0° C. to room temperature then the solvent was removed in vacuo and the residue was taken up in ethyl acetate (70 ml). The solution was washed with 0.3M KHSO$_4$ (2×20 ml), sat. NaHCO$_3$ (2×20 ml), water (2×20 ml) and brine (1×20 ml), dried (Na$_2$SO$_4$) and evaporated in vacuo. The residue was purified by flash chromatography on silica gel (eluant: 60% ethyl acetate, 40% pet. ether 60–80) to give a colourless oil identified as (2S)-1-[N$^\alpha$-(tert-butyloxycarbonyl)-N$^\omega$-(quinoxalinyl-2-carbonyl)-L-ornithinyl]pyrrolidine-2-carbonitrile (310 mg, 0.67 mmol, 69%).

5E. (2S)-1-[N$^\alpha$-(4'-Oxopent-2'-en-2'-yl)-N$^\omega$-(quinoxalinyl-2-carbonyl)-L-ornithinyl]-pyrrolidine-2-carbonitrile (2S)-1-[N$^\alpha$-(tert-Butyloxycarbonyl)-N$^\omega$-(quinoxalinyl-2-carbonyl)-L-ornithinyl]pyrrolidine-2-carbonitrile (160 mg, 0.34 mmol) was dissolved in trifluoroacetic acid (20 ml). The mixture was stirred for one hour at room temperature then the solvent was removed in vacuo. The residue was dissolved in dichloromethane (25 ml) and 2,4-pentanedione (48 mg, 0.48 mmol) and triethylamine (100 mg, 1.0 mmol) were added. The reaction was stirred at room temperature for 18 hours then evaporated in vacuo. The residue taken up in ethyl acetate (70 ml). The solution was washed with sat NaHCO$_3$, water and brine, dried (Na$_2$SO$_4$) and evaporated. The residue was purified by flash chromatography on silica gel (eluant: 98% chloroform, 2% methanol) to give a white solid identified as (2S)-1-[N$^\alpha$-(4'-oxopent-2'-en-2'-yl)-N$^\omega$-(quinoxalinyl-2-carbonyl)-L-ornithinyl]-pyrrolidine-2-carbonitrile (87 mg, 0.19 mmol, 57%).

[M+H]$^+$=449.2 $^1$H NMR (CDCl$_3$): δ 1.89–2.02 (10H,2× s+m), 2.13–2.24 (4H,m), 3.57–3.62 (5H,m), 4.3–4.6 (1H,m), 4.70–4.81 (1H,m), 5.02 (1H,s), 7.83–7.88 (2H,m), 8.10–8.19 (3H,m), 9.62 (1H,s), 11.0–11.2 (1H,m) ppm.

EXAMPLE 6

(2S)-1-[N-Acetoxymethoxycarbonyl-S-(3-picolyl-carbamoylmethyl)-L-cysteinyl]-pyrrolidine-2-carbonitrile

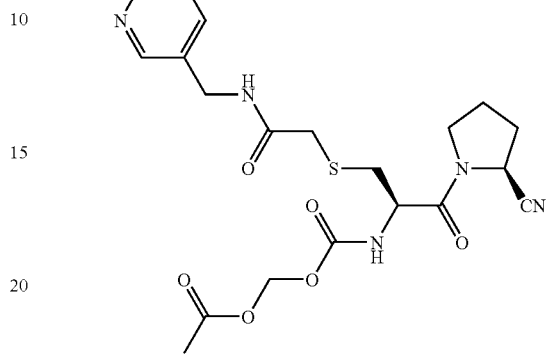

6A. S-(Benzyloxycarbonylmethyl)-N-(tert-butyloxycarbonyl)-L-cysteine

N-(tert-Butyloxycarbonyl)-L-cysteine (3.5 g, 15.8 mmol), benzyl 2-bromoacetate (3.7 g, 16.1 mmol) and triethylamine (1.8 g, 18.0 mmol) were dissolved in THF (100 ml). The mixture was stirred for 18 hours at room temperature then diluted with ethyl acetate (100 ml), washed with 0.3M KHSO$_4$, sat NaHCO$_3$, water and brine, dried (Na$_2$SO$_4$) and evaporated in vacuo. The residue was purified by flash chromatography on silica gel (eluant: 95% chloroform, 4% methanol, 1% acetic acid) to give a colourless oil identified as S-(benzyloxyrarbonylmethyl)-N-(tert-butyloxycarbonyl)-L-cysteine (5.2 g, 14.1 mmol, 89%).

6B. (2S)-1-[S-(Benzyloxycarbonylmethyl)-N-(tert-butyloxycarbonyl)-L-cysteinyl]-pyrrolidine-2-carbonitrile S-(Benzyloxycarbonylmethyl)-N-(tert-butyloxycarbonyl)-L-cysteine (5.10 g, 13.8 mmol) was dissolved in CH$_2$Cl$_2$ (200 ml). This solution was cooled to 0° C., (2S)-pyrrolidine-2-carbonitrile hydrochloride (2.1 g, 15.8 mmol) and PyBOP (8.0 g, 15.3 mmol) were added, and the pH adjusted to pH9 with triethylamine. The mixture was stirred for 18 h at 0° C. to room temperature then the solvent was removed in vacuo and the residue was taken up in ethyl acetate (150 ml). The solution was washed with 0.3M KHSO$_4$ (1×50 ml), sat. NaHCO$_3$ (1×50 ml), water (1×50 ml) and brine (1×50 ml), dried (Na$_2$SO$_4$) and evaporated in vacuo to give a yellow oil which was purified by flash chromatography on silica gel (eluant: 40% ethyl acetate, 60% pet. ether 60–80) to give a colourless oil identified as (2S)-1-[S-(benzyloxycarbonylmethyl)-N-(tert-butyloxycarbonyl)-L-cysteinyl]pyrrolidine-2-carbonitrile (5.82 g, 13.0 mmol, 94%).

6C. (2S)-1-[N-(tert-Butyloxycarbonyl)-S-(carboxymethyl)-L-cysteinyl]pyrrolidine-2-carbonitrile (2S)-1-[S-(Benzyloxycarbonylmethyl)-N-(tert-butyloxycarbonyl)-L-cysteinyl]pyrrolidine-2-carbonitrile (1.31 g, 2.9 mmol) was dissolved in THF(100 ml). 1M Lithium hydroxide (3.5 ml, 3.5 mmol) was added. The mixture was stirred for 3 hours at room temperature then with ethyl acetate (100 ml), washed with 1M citric acid, water and brine, dried (Na$_2$SO$_4$) and evaporated in vacuo to give a colourless oil which was purified by flash chromatography on silica gel (eluant: 97% chloroform, 2% methanol, 1% acetic acid) to give a colourless oil identified as (2S)-1-[N-(tert-butyloxycarbonyl)-S-(carboxymethyl)-L-cysteinyl]pyrrolidine-2-carbonitrile (860 mg, 2.4 mmol, 82%).

6D. (2S)-1-[N-(tert-Butyloxycarbonyl)-S-(3-picolylcarbamoylmethyl))-L-cysteinyl]-pyrrolidine-2-carbonitrile (2S)-1-[N-(tert-Butyloxycarbonyl)-S-(carboxymethyl)-L-cysteinyl]pyrrolidine-2-carbonitrile (150 mg, 0.42 mmol) was dissolved in CH$_2$Cl$_2$ (20 ml). The solution was cooled to 0° C., 3-(aminomethyl)pyridine (53 mg, 0.5 mmol) and PyBOP (270 mg, 0.52 mmol) were added, and the pH was adjusted to pH9 with triethylamine. The mixture was stirred for 18 h at 0° C. to room temperature then the solvent was removed in vacuo and the residue was dissolved in ethyl acetate (70 ml). The solution was washed with 0.3M KHSO$_4$ (1×20 ml), sat. NaHCO$_3$ (1×20 ml), water (1×20 ml) and brine (1×20 ml), dried (Na$_2$SO$_4$) and evaporated in vacuo to give a yellow oil which was purified by flash chromatography on silica gel (eluant: 96% chloroform, 4% methanol) to give a colourless oil identified as (2S)-1-[N-(tert-butyloxycarbonyl)-S-(3-picolylcarbamoylmethyl))-L-cysteinyl]pyrrolidine-2-carbonitrile (170 mg, 0.38 mmol, 91%).

6E. (2S)-1-[N$^\alpha$-Acetoxymethoxycarbonyl-S-(3-picolylcarbamoylmethyl)-L-cysteinyl]pyrrolidine-2-carbonitrile (2S)-1-[N-(tert-Butyloxycarbonyl)-S-(3-picolylcarbamoylmethyl)-L-cysteinyl]pyrrolidine-2-carbonitrile (130 mg, 0.29 mmol) was dissolved in trifluoroacetic acid (20 ml). The solution was stirred for 1 hour at room temperature then the solvent was removed in vacuo. The residue was dissolved in dichloromethane (25 ml) and acetoxymethyl p-nitrophenyl carbonate (80 mg, 0.31 mmol; prepared according to Alexander et al., J. Med. Chem. 31, 318, 1988) and triethylamine (40 mg, 0.4 mmol) were added. The solution was stirred at room temperature for 18 hours then evaporated in vacuo and the residue was taken up in ethyl acetate (70 ml). The solution was washed with sat NaHCO$_3$, water and brine, dried (Na$_2$SO$_4$) and evaporated. The residue was purified by flash chromatography on silica gel (eluant: 90% ethyl acetate, 10% pet. ether 60–80) to give a white solid identified as (2S)-1-[N$^\alpha$-acetoxymethoxycarbonyl-S-(3-picolylcarbamoylmethyl)-L-cysteinyl]pyrrolidine-2-carbonitrile (33 mg, 0.071 mmol, 24%).

[M+H]$^+$=464.0 $^1$H NMR (CDCl$_3$): δ 2.08 (3H,s), 2.13–2.29 (4H,m), 2.89 (2H,d,J=6.9 Hz), 3.20–3.29 (2H,m), 3.61–3.74 (2H,m), 4.46 (2H,d,J=5.9 Hz), 4.60–4.71 (2H,m), 5.68 (2H,s), 6.12 (1H,d,J=8.6 Hz), 7.16–7.27 (2H,m), 7.66 (1H,d,J=8.1 Hz), 8.50 (1H,d,J=4.7 Hz), 8.56 (1H,s) ppm.

EXAMPLE 7

3-[N$^\alpha$-(1'-Acetoxyethoxycarbonyl)-N$^\omega$-(5,6-dichloronicotinoyl)-L-ornithinyl]-thiazolidine

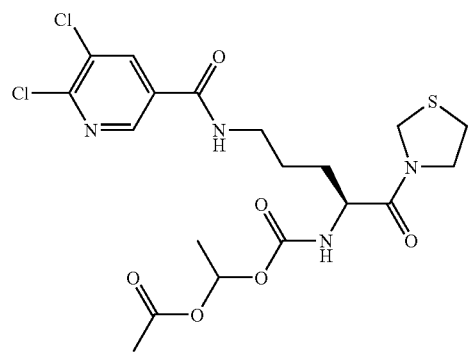

7A. 3-[N$^\alpha$-(tert-Butyloxycarbonyl)-N$^\omega$-(9-fluorenylmethyloxycarbonyl)-L-ornithinyl]thiazolidine N$^\alpha$-(tert-Butyloxycarbonyl)-N$^\omega$-(9-fluorenylmethyloxycarbonyl)-L-ornithine (2.73 g, 6 mmol) was dissolved in CH$_2$Cl$_2$/DMF (9:1, 100 ml). To this solution at 0° C. were added 1-hydroxybenzotriazole hydrate (1.53 g, 10 mmol), water-soluble carbodiimide (1.34 g, 7 mmol), thiazolidine (1.28 g, 18 mmol) and triethylamine (80 mg, 8 mmol). The mixture was stirred for 18 h at 0° C. to room temperature then the solvent was removed in vacuo and the residue was taken up in ethyl acetate (100 ml). The solution was washed with 0.3M KHSO$_4$ (2×25 ml), sat. NaHCO$_3$ (2×25 ml), water (2×25 ml) and brine (1×25 ml), dried (Na$_2$SO$_4$) and evaporated in vacuo. The residue was purified by flash chromatography on silica gel (eluant: 75% ethyl acetate, 25% pet. ether 60–80) to give a white solid identified as 3-[N$^\alpha$-(tert-butyloxycarbonyl)-N$^\omega$-(9-fluorenylmethyloxycarbonyl)-L-ornithinyl]thiazolidine (2.55 g, 4.85 mmol, 81%).

7B. 3-[N$^\alpha$-(tert-Butyloxycarbonyl)-L-ornithinyl]thiazolidine

3-[N$^\alpha$-(tert-Butyloxycarbonyl)-N$^\omega$-(9-fluorenylmethyloxycarbonyl)-L-ornithinyl]thiazolidine (1.15 g, 2.13 mmol) was dissolved in acetonitrile (20 ml). Diethylamine (5 ml) was added. The mixture was stirred for 90 min at room temperature then the solvent was removed in vacuo and the residue was purified by flash chromatography on silica gel (eluant: 90% chloroform, 7% methanol, 3% triethylamine) to give a pale yellow oil identified as 3-[N$^\alpha$-(tert-butyloxycarbonyl)-L-ornithinyl]thiazolidine (530 mg, 1.67 mmol, 78%).

7C. 3-[N$^\alpha$-(tert-Butyloxycarbonyl)-N$^\omega$-(5,6-dichloronicotinoyl)-L-omithinyl]-thiazolidine 3-[N$^\alpha$-(tert-Butyloxycarbonyl)-L-ornithinyl]thiazolidine (600 mg, 1.96 mmol) was dissolved in CH$_2$Cl$_2$/DMF (9:1, 50 ml). To this solution at 0° C. were added 1-hydroxybenzotriazole hydrate (360 mg, 2.36 mmol), water-soluble carbodiimide (472 mg, 2.36 mmol), 5,6-dichloronicotinic acid (416 mg, 2.16 mmol) and triethylamine (360 mg, 3.6 mmol).

The mixture was stirred for 18 h at 0° C. to room temperature then the solvent was removed in vacuo and the residue was taken up in ethyl acetate (70 ml). The solution was washed with 0.3M KHSO$_4$ (2×20 ml), sat. NaHCO$_3$ (2×20 ml), water (2×20 ml) and brine (1×20 ml), dried (Na$_2$SO$_4$) and evaporated in vacuo. The residue was purified by flash chromatography on silica gel (eluant: 2% methanol, 98% chloroform) to give a sticky white solid identified as 3-[N$^\alpha$-(tert-butyloxycarbonyl)-N$^\omega$-(5,6-dichloronicotinoyl)-L-ornithinyl]thiazolidine (512 mg, 1.08 mmol, 56%).

7D. 3-[N$^\alpha$-(1'-Acetoxyethoxycarbonyl)-N$^\omega$-(5,6dichloronicotinoyl)-L-ornithinyl]-thiazolidine 3-[N$^\alpha$-(tert-Butyloxycarbonyl)-N$^\omega$-(5,6-dichloronicotinoyl)-L-ornithinyl]thiazolidine (128 mg, 0.27 mmol) was dissolved in 4M HCl/dioxan (20 ml). The mixture was stirred for 1 hour at room temperature then the solvent was removed in vacuo. The residue was dissolved in dichloromethane (25 ml) and α-acetoxyethyl p-nitrophenyl carbonate (83 mg, 0.3 mmol; prepared according to Alexander et al., J. Med. Chem. 31, 318, 1988) and triethylamine (40 mg, 0.4 mmol) were added. The solution was stirred at room temperature for 18 hours then evaporated in vacuo. The residue was taken up in ethyl acetate (70 ml). The solution was washed with sat NaHCO$_3$, water and brine, dried (Na$_2$SO$_4$) and evaporated. The residue was purified by flash chromatography on silica gel (eluant: 75% ethyl acetate, 25% pet. ether 60–80) to give a white solid identified as 3-[N$^\alpha$-(1'-acetoxyethoxycarbonyl)-N$^\omega$-(5,6-dichloronicotinoyl)-L-ornithinyl]thiazolidine (67 mg, 0.13 mmol, 47%).

[M+H]$^+$=509.0 $^1$H NMR (CDCl$_3$): δ 1.44–1.46 (3H, m), 1.63–1.99 (3H,br m), 1.99–2.04 (4H,m), 2.98–3.06 (2H,m), 3.46–3.48 (2H,m), 3.50–3.80 (2H,m), 4.47–4.56 (3H,m), 5.81–5.91 (1H,m), 6.74–6.75 (1H,m), 7.24–7.33 (1H,m), 8.24–8.25 (1H,m), 8.69–8.71 (1H,m) ppm.

EXAMPLE 8

3-[N$^\alpha$-Methoxycarbonyl-N$^\omega$-(6-trifluoromethyinicotinoyl)-L-ornithinyl]thiazolidine

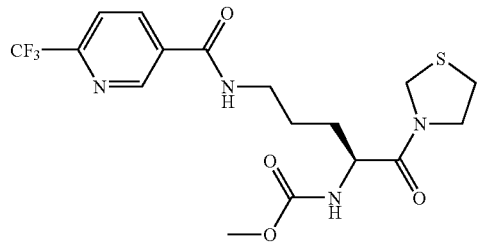

8A. 3-[N$^\alpha$-(tert-Butyloxycarbonyl)-N$^\omega$-(6-trifluoromethylnicotinoyl)-L-ornithinyl]-thiazolidine 3-[N$^\alpha$-(tert-Butyloxycarbonyl)-L-ornithinyl]thiazolidine (150 mg, 0.49 mmol) was dissolved in CH$_2$Cl$_2$/DMF (9:1, 20 ml). To this solution at 0° C. were added 1-hydroxybenzotriazole hydrate (100 mg, 0.74 mmol), water-soluble carbodiimide (118 mg, 0.59 mmol), 6-trifluoromethylnicotinic acid (104 mg, 0.54 mmol) and triethylamine (100 mg, 1.0 mmol). The mixture was stirred for 18 h at 0° C. to room temperature then the solvent was removed in vacuo and the residue was taken up in ethyl acetate (70 ml). The solution was washed with 0.3M KHSO$_4$ (2×20 ml), sat. NaHCO$_3$ (2×20 ml), water (2×20 ml) and brine (1×20 ml), dried (Na$_2$SO$_4$) and evaporated in vacuo. The residue was purified by flash chromatography on silica gel (eluant: 6% methanol, 94% chloroform) to give a sticky white solid identified as 3-[N$^\alpha$-(tert-butyloxycarbonyl)-N$^\omega$-(6-trifluoromethyinicotinoyl)-L-ornithinyl]thiazolidine (76 mg, 0.16 mmol, 32%).

8B. 3-[N$^\alpha$-Methoxycarbonyl-N$^\omega$-(6-trifluoromethyinicotinoyl)-L-ornithinyl]-thiazolidine 3-[N$^\alpha$-(tert-Butyloxycarbonyl)-N$^\omega$-(6-trifluoromethylnicotinoyl)-L-ornithinyl]thiazolidine (76 mg, 0.16 mmol) was dissolved in 4M HCl/dioxan (20 ml). The mixture was stirred for 1 hour at room temperature then the solvent was removed in vacuo. The residue was dissolved in dichloromethane (25 ml) and methyl chloroformate (17 mg, 0.18 mmol) and triethylamine (20 mg, 0.2 mmol) were added. The solution was stirred at room temperature for 18 hours then evaporated in vacuo. The residue was taken up in ethyl acetate (70 ml). The solution was washed with sat NaHCO$_3$, water and brine, dried (Na$_2$SO$_4$) and evaporated. The residue was purified by flash chromatography on silica gel (eluant: 3% methanol, 97% chloroform) to give a white solid identified as 3-[N$^\alpha$-methoxycarbonyl-N$^\omega$-(6-trifluoromethyinicotinoyl)-L-ornithinyl]thiazolidine (66 mg, 0.15 mmol, 96%).

[M+H]$^+$=435.1 $^1$H NMR (CDCl$_3$): δ 1.36–1.79 (4H,m), 2.98–3.11 (2H,m), 3.48–3.60 (2H,m), 3.64 (3H,s), 3.72–4.10 (3H,m), 4.57–4.60 (2H,m), 5.63–5.76 (1H,m), 6.55 (1H,br m), 7.54–7.55(1H,m), 8.77–8.79 (2H,m) ppm.

EXAMPLE 9

3-[N$^\omega$-(5,6-Dichloronicotinoyl)-N$^\alpha$-(4'-oxopent-2'-en-2'-yl)-L-ornithinyl]thiazolidine

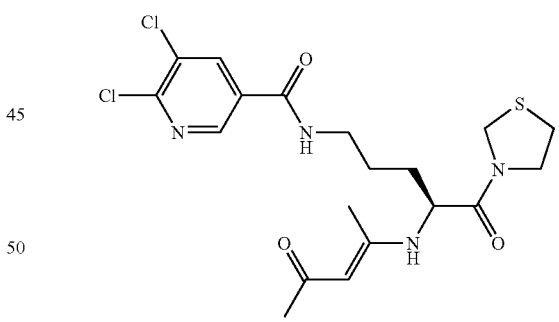

3-[N$^\alpha$-(tert-Butyloxycarbonyl)-N$^\omega$-(5,6-dichloronicotinoyl)-L-ornithinyl]thiazolidine (162 mg, 0.34 mmol) was dissolved in 4M HCl/dioxan (20 ml). The mixture was stirred for 1 hour at room temperature then the solvent was removed in vacuo. The residue was dissolved in dichloromethane (25 ml) and 2,4-pentanedione (100 mg, 0.37 mmol) and triethylamine (40 mg, 0.4 mmol) were added. The solution was stirred at room temperature for 18 hours then evaporated in vacuo. The residue was taken up in ethyl acetate (70 ml). The solution was washed with sat NaHCO$_3$, water and brine, dried (Na$_2$SO$_4$) and evaporated. The residue was purified by flash chromatography on silica gel (eluant: 90% ethyl acetate, 10% pet. ether 60–80) to give a white solid identified as 3-[N^ω-(5,6-dichloronicotinoyl)-N^(α-4')-oxopent-2'-en-2'-yl)-L-ornithinyl]thiazolidine (63 mg, 0.14 mmol, 40%).

[M+H]⁺=461.3 ¹H NMR (CDCl₃): δ 1.74–1.86 (6H,m), 1.87 (3H,s), 1.97 (3H,s), 2.94–3.11 (2H,m), 3.46–3.51 (2H,m), 3.75–3.79 (1H,m), 4.48–4.57 (2H,m), 5.01 (1H,s), 7.60–7.90 (1H,m), 8.34 (1H,d,J=2.0 Hz), 8.78 (1H,d,J=2.3 Hz), 11.01 (1H,d,J=8.2 Hz) ppm.

EXAMPLE 10

3-[N^α-(Acetoxymethoxycarbonyl)-N^ω-(3,4dichlorobenzyl)-L-glutaminyl]thiazolidine

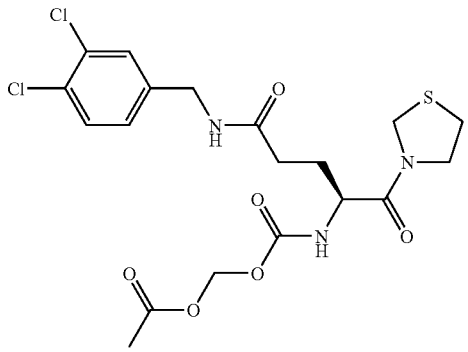

10A. 3-[N-(tert-Butyloxycarbonyl)-O^ω-methyl-L-glutamyl]thiazolidine

N-(tert-Butyloxycarbonyl)-O^ω-methyl-L-glutamic acid (6.28 g, 24 mmol) was dissolved in CH₂Cl₂/DMF (9:1, 100 ml). To this solution at 0° C. were added 1-hydroxybenzotriazole hydrate (5.5 g, 36 mmol), water-soluble carbodiimide (5.38 g, 28 mmol), thiazolidine (2.48 g, 28 mmol) and triethylamine (3.0 g, 30 mmol). The mixture was stirred for 18 h at 0° C. to room temperature then the solvent was removed in vacuo and the residue was taken up in ethyl acetate (150 ml). The solution was washed with 0.3M KHSO₄ (2×30 ml), sat. NaHCO₃ (2×30 ml), water (2×30 ml) and brine (1×30 ml), dried (Na₂SO₄) and evaporated in vacuo. The residue was purified by flash chromatography on silica gel (eluant: 70% ethyl acetate, 30% pet. ether 60–80) to give a brown oil identified as 3-[N-(tert-butyloxycarbonyl)-O^ω-methyl-L-glutamyl]thiazolidine (4.0 g, 12 mmol, 50%).

10B. 3-[N-(tert-Butyloxycarbonyl)-L-glutamyl]thiazolidine

3-[N-(tert-Butyloxycarbonyl)-O^ω-methyl-L-glutamyl]thiazolidine (3.23 g, 9.73 mmol) was dissolved in THF (50 ml). 1M Lithium hydroxide (11 ml, 11 mmol) was added. The mixture was stirred for 1 hour at room temperature then the solvent was removed in vacuo and the residue was taken up in ethyl acetate (70 ml). The solution was washed with 1M KHSO₄ (2×20 ml), water (2×20 ml) and brine (1×20 ml), dried (Na₂SO₄) and evaporated in vacuo to give a colourless oil identified as 3-[N-(tert-butyloxycarbonyl)-L-glutamyl]thiazolidine (3.0 g, 9.4 mmol, 97%).

10C. 3-[N^α-(tert-Butyloxycarbonyl)-N^ω-(3,4dichlorobenzyl)-L-glutaminyl]-thiazolidine 3-[N-(tert-Butyloxycarbonyl)-L-glutamyl]thiazolidine (200 mg, 0.63 mmol) was dissolved in CH₂Cl₂/DMF (9:1, 10 ml). To this solution at 0° C. was added 1-hydroxybenzotriazole hydrate (119 mg, 0.76 mmol), water-soluble carbodiimide (163 mg, 0.88 mmol), 3,4-dichlorobenzylamine (111 mg, 0.83 mmol) and triethylamine(126 mg, 1.26 mmol). The mixture was stirred for 18 h at 0° C. to room temperature then the solvent was removed in vacuo and the residue was taken up in ethyl acetate (70 ml). The solution was washed with 0.3M KHSO₄ (2×20 ml), sat. NaHCO₃ (2×20 ml), water (2×20 ml) and brine (1×20 ml), dried (Na₂SO₄) and evaporated in vacuo to give a yellow oil. The residue was purified by flash chromatography on silica gel (eluant: ethyl acetate) to give a colourless oil identified as 3-[N^α-(tert-butyloxycarbonyl)-N^ω-(3,4-dichlorobenzyl)-L-glutaminyl]thiazolidine (295 mg, 0.62 mmol, 98%).

10D. 3-[N^α-(Acetoxymethoxycarbonyl)-N^ω-(3,4-dichlorobenzyl)-L-glutaminyl]-thiazolidine 3-[N^α-(tert-Butyloxycarbonyl)-N^ω-(3,4dichlorobenzyl)-L-glutaminyl]thiazolidine (150 mg, 0.32 mmol) was dissolved in 4M HCl/dioxan (20 ml). The mixture was stirred for 1 hour at room temperature then the solvent was removed in vacuo. The residue was dissolved in dichloromethane (25 ml) and acetoxymethyl p-nitrophenyl carbonate (95 mg, 0.35 mmol; prepared according to Alexander et al., J. Med. Chem. 31, 318, 1988) and triethylamine (64 mg, 0.64 mmol) were added. The solution was stirred at room temperature for 18 hours then evaporated in vacuo. The residue taken up in ethyl acetate (70 ml). The solution was washed with sat NaHCO₃, water and brine, dried (Na₂SO₄) and evaporated. The residue was purified by flash chromatography on silica gel (eluant: ethyl acetate) to give a white solid identified as 3-[N^α-(acetoxymethoxycarbonyl)-N^ω-(3,4-dichlorobenzyl)-L-glutaminyl]thiazolidine (88 mg, 0.18 mmol, 56%).

[M+H]⁺=492.0 ¹H NMR (CDCl₃): δ 1.44–1.46 (3H,m), 1.63–1.99 (3H,br m), 1.99–2.04 (4H,m), 2.98–3.06 (2H,m), 3.46–3.48 (2H,m), 3.50–3.80 (2H m), 4.47–4.56 (3H,m), 5.81–5.91 (1H,m), 6.74–6.75 (1H,m), 7.24–7.33 (1H,m), 8.24–8.25 (1H,m), 8.69–8.71 (1H,m) ppm.

EXAMPLE 11

1-[N^α-(1'-Acetoxyethoxycarbonyl)-N^ω-(2chloronicotinoyl)-L-ornithinyl]pyrrolidine

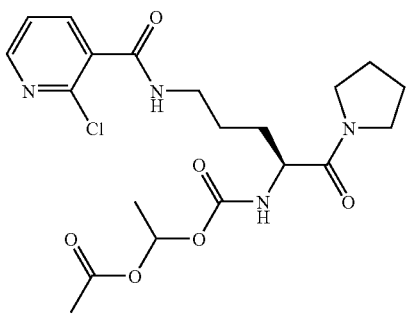

11A. 1-[N^ω-(Benzyloxycarbonyl)-N^α-(tert-butyloxycarbonyl)-L-ornithinyl]pyrrolidine N^ω-(Benzyloxycarbonyl)-N^α-(tert-butyloxycarbonyl)-L-ornithine (5.49 g, 15 mmol) was dissolved in CH₂Cl₂/DMF (9:1, 100 ml). To this solution at 0° C. were added 1-hydroxybenzotriazole hydrate (3.37 g, 22 mmol), water-soluble carbodiimide (3.46 g, 18 mmol), pyrrolidine (1.28 g, 18 mmol) and triethylamine (200 mg, 20 mmol). The mixture was stirred for 18 h at 0° C. to room temperature then the solvent was removed in vacuo and the residue was taken up in ethyl acetate (200 ml). The solution was washed with 0.3M $KHSO_4$ (2×50 ml), sat. $NaHCO_3$ (2×50 ml), water (2×50 ml) and brine (1×50 ml), dried ($Na_2SO_4$) and evaporated in vacuo. The residue was purified by flash chromatography on silica gel (eluant: 90% ethyl acetate, 10% pet. ether 60–80) to give a colourless oil identified as 1-[$N^\omega$-(benzyloxycarbonyl)-$N^\alpha$-(tert-butyloxycarbonyl)-L-ornithinyl]pyrrolidine (5.15 g, 12.3 mmol, 82%).

11B. 1-[$N^\alpha$-(tert-Butyloxycarbonyl)-L-ornithinyl]pyrrolidine

To a solution of 1-[$N^\omega$-(benzyloxycarbonyl)-$N^\alpha$-(tert-butyloxycarbonyl)-L-ornithinyl]-pyrrolidine (2.15 g, 5.13 mmol) in methanol (80 ml) was added 10% Pd/C (400 mg). The mixture was stirred under a hydrogen atmosphere for 2 hours then the catalyst was filtered off and washed with methanol (50 ml). The combined filtrates were evaporated in vacuo to give an off white solid identified as 1-[$N^\alpha$-(tert-butyloxycarbonyl)-L-ornithinyl]pyrrolidine (1.35 g, 4.74 mmol, 94%).

11C. 1-[$N^\alpha$-(tert-Butyloxycarbonyl)-$N^\omega$-(2-chloronicotinoyl)-L-ornithinyl]pyrrolidine 1-[$N^\alpha$-(tert-Butyloxycarbonyl)-L-ornithinyl]pyrrolidine (204 mg, 0.72 mmol) was dissolved in $CH_2Cl_2$ (20 ml). To this solution was added 2-chloronicotinoyl chloride (130 mg, 0.74 mmol) and triethylamine (200 mg, 2.0 mmol). The mixture was stirred for 18 h at 0° C. to room temperature then the solvent was removed in vacuo and the residue was taken up in ethyl acetate (70 ml). The solution was washed with 0.3M $KHSO_4$ (2×20 ml), sat. $NaHCO_3$ (2×20 ml), water (2×20 ml) and brine (1×20 ml), dried ($Na_2SO_4$) and evaporated in vacuo. The residue was purified by flash chromatography on silica gel (eluant: 10% methanol, 90% chloroform) to give a sticky white solid identified as 1-[$N^\alpha$-(tert-butyloxycarbonyl)-$N^\omega$-(2-chloronicotinoyl)-L-ornithinyl]pyrrolidine (236 mg, 0.56 mmol, 78%).

11D. 1-[$N^\alpha$-(1'-Acetoxyethoxycarbonyl)-$N^\omega$-(2-chloronicotinoyl)-L-ornithinyl]-pyrrolidine 1-[$N^\alpha$-(tert-Butyloxycarbonyl)-$N^\omega$-(2-chloronicotinoyl)-L-ornithinyl]pyrrolidine (206 mg, 0.49 mmol) was dissolved in 4M HCl/dioxan (20 ml). The mixture was stirred for 1 hour at room temperature then the solvent was removed in vacuo. The residue was dissolved in dichloromethane (25 ml) and α-acetoxyethyl p-nitrophenyl carbonate (140 mg, 0.52 mmol; prepared according to Alexander et al., J. Med. Chem. 31, 318, 1988) and triethylamine (40 mg, 0.4 mmol) were added. The solution was stirred at room temperature for 18 hours then evaporated in vacuo. The residue was taken up in ethyl acetate (70 ml). The solution was washed with sat $NaHCO_3$, water and brine, dried ($Na_2SO_4$) and evaporated. The residue was purified by flash chromatography on silica gel (eluant: 92% chloroform, 8% methanol) to give a white solid identified as 1-[$N^\alpha$-(1'-acetoxyethoxycarbonyl)-$N^\omega$-(2-chloronicotinoyl)-L-omithinyl]pyrrolidine (127 mg, 0.28 mmol, 57%).

[M+H]$^+$=455.1 $^1$H NMR (CDCl$_3$): δ 1.42–1.49 (3H,m), 1.83–1.95 (8H,m), 2.02 (3H,d,J=1.5 Hz), 3.32–3.71 (6H,m), 4.45–4.47 (1H,m), 5.75–5.85 (1H,m), 6.72–6.77 (2H,m), 7.27–7.33 (1H,m), 7.97–8.06 (1H,m), 8.40–8.43 (1H,m) ppm.

The invention claimed is:
1. A compound according to general formula 1

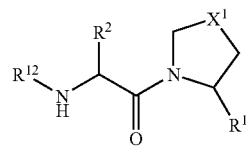

or a pharmaceutically acceptable salt thereof, wherein:
$R^1$ is H or CN,
$R^2$ is selected from $CH_2R^5$, $CH_2CH_2R^5$ and $C(R^3)(R^4)$—$X^2$—$(CH_2)_aR^5$,
$R^3$ and $R^4$ are each H;
$R^5$ is selected from $N(R^8)C(=O)R^9$, $N(R^8)C(=S)R^9$ and $N(R^8)R^{10}$;
$R^8$ is H;
$R^9$ is $R^{11}(CH_2)_b$;
$R^{10}$ is $R^{11}(CH_2)_b$;
$R^{11}$ is heteroaryl;
$R^{12}$ is $R^{19}OC(=O)$;
$R^{19}$ is $R^{20}C(=O)OC(R^{21})(R^{22})$;
$R^{20}$, $R^{21}$ and $R^{22}$ are each independently selected from H and lower alkyl ($C_1$–$C_6$);
$X^1$ is $CH_2$,
$X^2$ is $CH_2$;
a is 1, 2 or 3 and
b is 0–3.

2. A compound according to claim 1 wherein $R^2$ is selected from $CH_2CH_2R^5$ and $C(R^3)(R^4)$—$X^2$—$(CH_2)_aR^5$.

3. A compound according to claim 1 wherein $R^2$ is selected from $CH_2CH_2CH_2R^5$ and $CH_2CH_2CH_2CH_2R^5$.

4. A pharmaceutical composition comprising a compound according to claim 1.

5. A compound according to claim 1, where a is 1 and b is 0.

6. A compound according to claim 1, wherein the compound is (2S)-1-[$N^\alpha$-(1'-Acetoxyethoxycarbonyl)-$N^\omega$-(pyrazinyl-2-carbonyl)-L-ornithinyl]-pyrrolidine-2-carbonitrile.

7. A compound according to claim 1, wherein the compound is 1-[$N^\alpha$-(1'-Acetoxyethoxycarbonyl)-$N^\omega$-(2-chloronicotinoyl)-L-ornithinyl]pyrrolidine.

* * * * *